United States Patent
Peleg et al.

(10) Patent No.: US 9,536,296 B2
(45) Date of Patent: Jan. 3, 2017

(54) IMAGING FOR QUALITY CONTROL IN AN ELECTRONIC CIGARETTE

(71) Applicant: SIS Resources, Ltd., Beit Shemesh (IL)

(72) Inventors: Eyal Peleg, Tsoran (IL); Bernard Juster, Netanya (IL)

(73) Assignee: SIS RESOURCES, LTD., Beit Shemesh (IL)

( * ) Notice: Subject to any disclaimer, the term of this patent is extended or adjusted under 35 U.S.C. 154(b) by 502 days.

(21) Appl. No.: 14/161,209

(22) Filed: Jan. 22, 2014

(65) Prior Publication Data

US 2014/0202474 A1     Jul. 24, 2014

Related U.S. Application Data

(60) Provisional application No. 61/755,008, filed on Jan. 22, 2013.

(51) Int. Cl.
| | |
|---|---|
| *G06T 7/00* | (2006.01) |
| *A24F 47/00* | (2006.01) |
| *H04N 5/33* | (2006.01) |
| *A24C 5/34* | (2006.01) |
| *G01N 25/72* | (2006.01) |

(52) U.S. Cl.
CPC ............ *G06T 7/0008* (2013.01); *A24C 5/3412* (2013.01); *A24F 47/008* (2013.01); *H04N 5/33* (2013.01); *G01N 25/72* (2013.01)

(58) Field of Classification Search
CPC ...... A24F 47/008; G01N 25/72; G06T 7/0008
See application file for complete search history.

(56) References Cited

U.S. PATENT DOCUMENTS

| | | | |
|---|---|---|---|
| 7,568,833 B2* | 8/2009 | Lopez Martinez ... | G01J 5/0003 374/121 |
| 2010/0167288 A1* | 7/2010 | Gale ................ | B01L 3/502707 435/6.19 |

FOREIGN PATENT DOCUMENTS

JP     2009-238375 A     10/2009

OTHER PUBLICATIONS

International Search Report (PCT/ISA/210) and Written Opinion of the International Searching Authority (PCT/ISA/237) for International Application No. PCT/IL2014/050078 dated Jun. 4, 2014.
Database WPI Week 200969 Thomson Scientific, London, GB; AN 2009-P81750 XP002723921, & JP 2009 238375 A (Mitsui Eng &Shipbuilding Co Ltd) Oct. 15, 2009 (Oct. 15, 2009).
Schripp T et al: "Does e-cigarette consumption cause passive vaping?", Indoor Air, vol. 23, No. 1, Jul. 2, 2012 (Jul. 2, 2012), pp. 25-31.

\* cited by examiner

*Primary Examiner* — Marcus Taningco
(74) *Attorney, Agent, or Firm* — Harness, Dickey & Pierce, P.L.C.

(57) ABSTRACT

Assembly and quality of an electronic cigarette ("e-Cig") may be tested and verified using imaging techniques. Infrared ("IR") imaging may identify whether a temperature is uniform in an e-Cig during usage. Potential burning locations may be identified through the imaging by identifying locations whose temperature is unusually high or non-uniform. This temperature information may be used to calibrate the power of the e-Cig.

19 Claims, 6 Drawing Sheets

IMAGING FOR QUALITY CONTROL IN AN ELECTRONIC CIGARETTE

PRIORITY

This application claims priority to U.S. Provisional Application No. 61/755,008, entitled "IR imaging for uniformity and correct assembly for electronic cigarettes," filed on Jan. 22, 2013, the entire disclosure of which is hereby incorporated by reference.

BACKGROUND

An electronic cigarette ("e-cigarette" or "e-Cig") is a device that emulates tobacco cigarette smoking, by producing smoke replacement that may be similar in its physical sensation, general appearance, and sometimes flavor (i.e., with tobacco fragrance, menthol taste, added nicotine etc.). The e-Cig may include a battery portion and a cartomizer portion (i.e. "cartridge"). The battery portion of the e-Cig includes a controller and battery for powering the device and the cartomizer portion generates an aerosol mist (i.e. e-smoke or vapor) that is a replacement for cigarette smoke. In particular, the cartomizer may use heat, ultrasonic energy, or other means to atomize/vaporize an "e-Liquid" solution (e.g. based on propylene glycol, or glycerin, for example including taste and fragrance ingredients) into an aerosol mist. The atomization may be similar to nebulizer or humidifier vaporizing solutions for inhalation. The cartomizer may include, or may be referred to as an atomizer, and the atomization may be caused by a heating element that heats the e-Liquid to generate the mist/vapor/e-smoke. The heating element may become quite hot in order to properly heat the e-Liquid and depending on the duration of usage of the e-Cig. Excessive heat within the e-Cig may cause burning of the internal components of the e-Cig. For example, burning may occur when a cartridge filled with a liquid becomes empty, such as when the liquid has evaporated or been vaporized as part of the e-Cig smoking process. Burning may result in bad taste and less pleasure when smoking and a smoker of an e-Cig may not be able to predict when the burning will occur. Calibration of the power provided from the battery to the cartridge may reduce the chances of burning.

BRIEF DESCRIPTION OF THE DRAWINGS

The system and method may be better understood with reference to the following drawings and description. Non-limiting and non-exhaustive embodiments are described with reference to the following drawings. The components in the drawings are not necessarily to scale, emphasis instead being placed upon illustrating the principles of the invention. In the drawings, like referenced numerals designate corresponding parts throughout the different views.

DETAILED DESCRIPTION

The system and method described herein describe an electronic cigarette ("e-Cig") testing system and method. In particular, imaging may be used for determining a temperature distribution of components in the cartridge, such as the coil. Excessively high temperatures or non-uniformity of temperature may indicate a potential problem for the cartridge and can be used to calibrate the cartridge. The calibration may include reducing power to the cartridge to determine if the temperature or uniformity improves. The optimal power level may then be determined.

Other systems, methods, features and advantages will be, or will become, apparent to one with skill in the art upon examination of the following figures and detailed description. It is intended that all such additional systems, methods, features and advantages be included within this description, be within the scope of the invention, and be protected by the following claims. Nothing in this section should be taken as a limitation on those claims. Further aspects and advantages are discussed below.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

Figure 1:
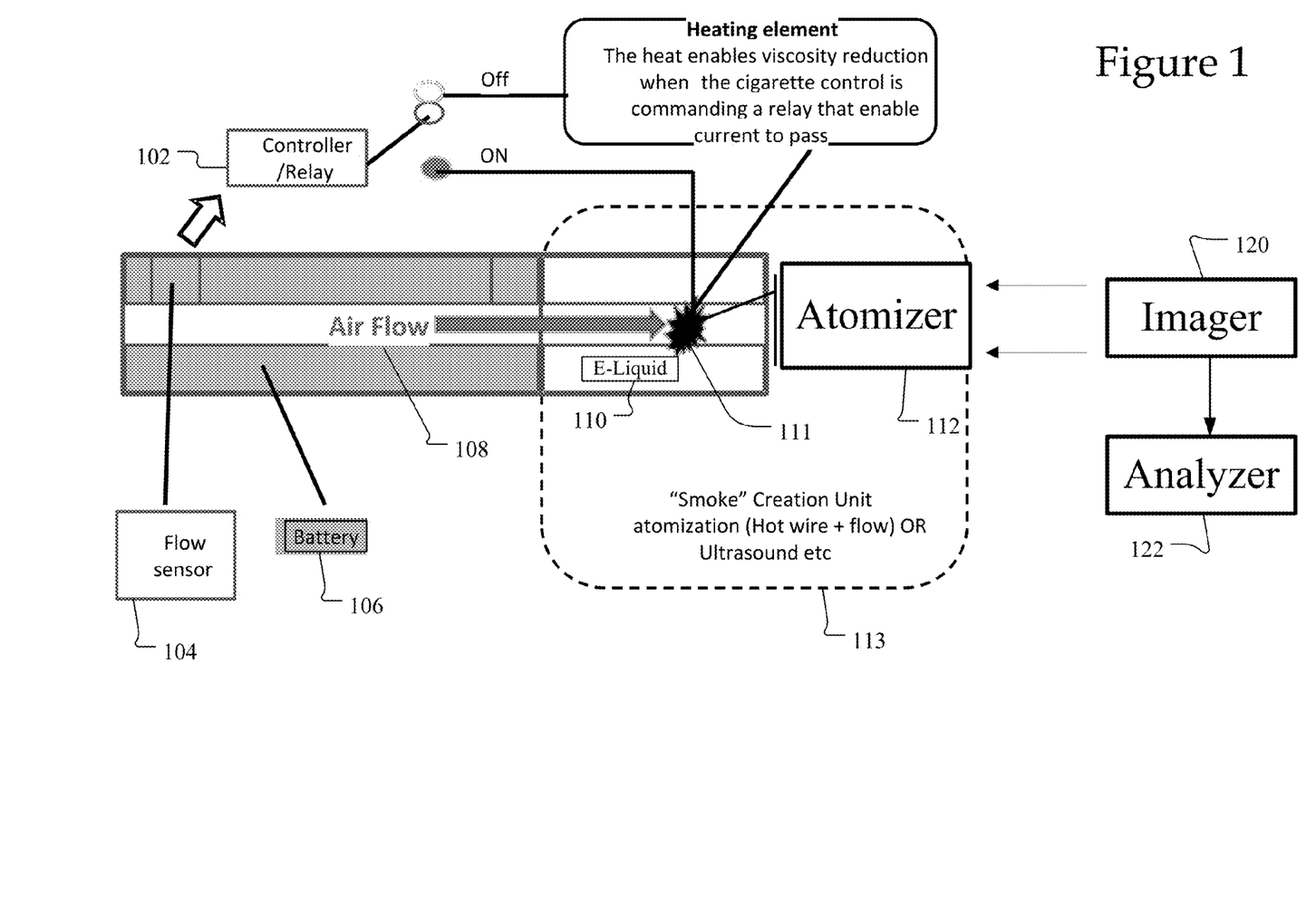
FIG. 1 is a diagram of an electronic cigarette.
Figure 2:
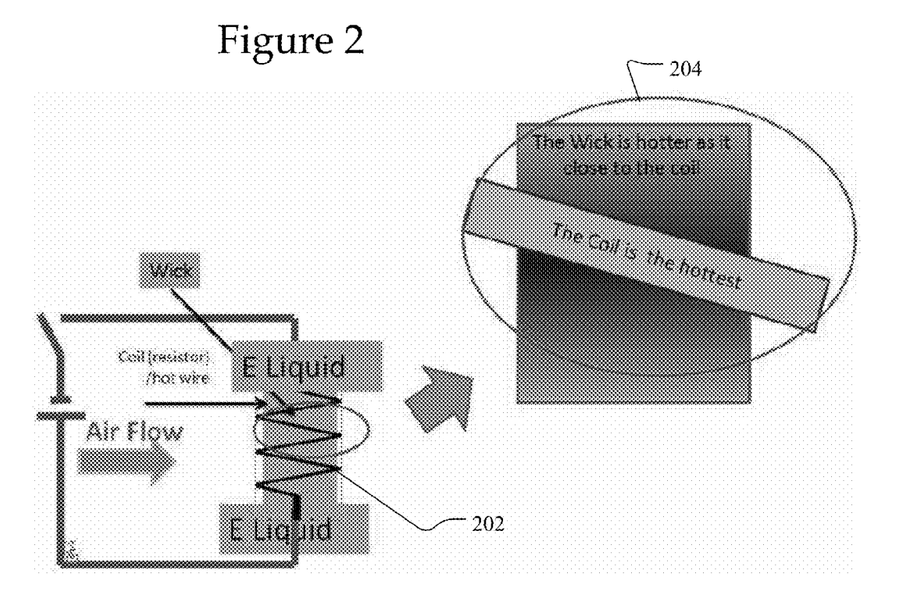
FIG. 2 is a diagram of a portion of the cartridge of an electronic cigarette.
Figure 3:
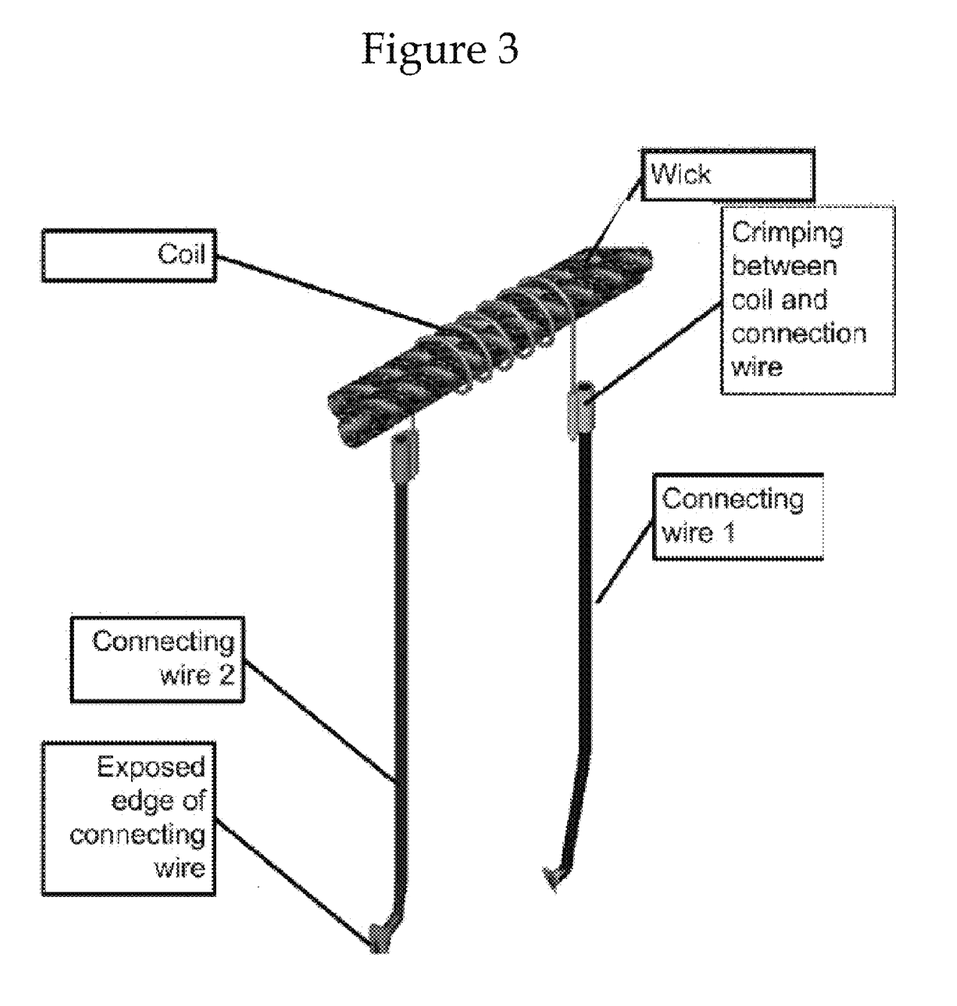
FIG. 3 is a diagram of the coil and wick for an electronic cigarette.
Figure 4:
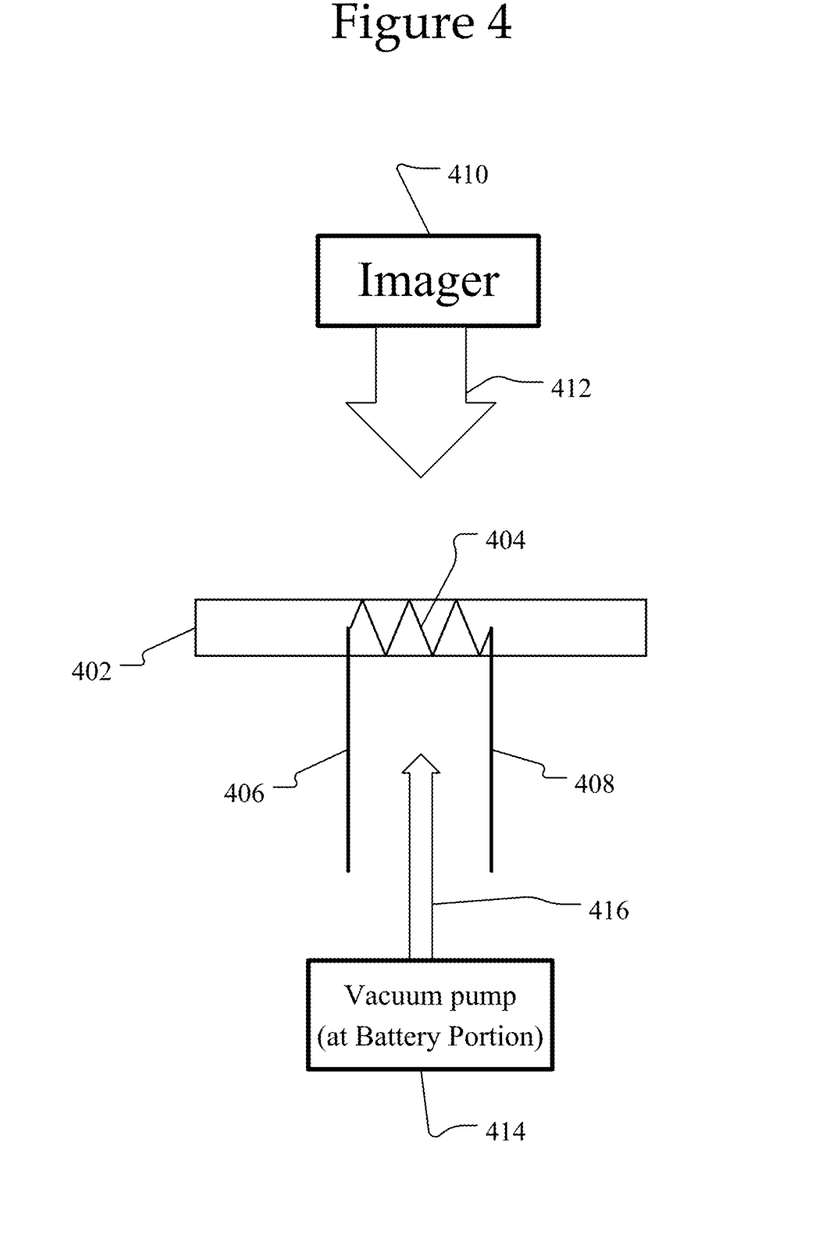
FIG. 4 is a diagram of an embodiment of imaging of an electronic cigarette.

FIG. 1 is a diagram of an electronic cigarette. The "smoke" produced by an e-Cig is a created by turning an e-Liquid 110 into mist and some vapor with an atomizer 112. The e-Liquid 110 may be stored in a liquid container. The cartomizer 113 may include the atomizer 112 and the e-Liquid 110. The cartomizer 113 may also be referred to as a cartridge throughout this disclosure and may be disposable. The e-liquid 110 may have a high viscosity at room temperature to enable longer shelf life and reduce leakages; however, this high viscosity may reduce the atomization rate. The e-Liquid is atomized via airflow 108, generated by the inhalation of the user (i.e. the smoker or consumer or vapor). In order to reduce the viscosity, to a level enabling atomization, external heat may be applied through the heating element 111, which may include a heating coil and a wick that is soaked in or includes a portion of the e-Liquid 110. An exemplary heating element is shown in FIGS. 2-4. In particular, the heating element 111 may be a coil in one embodiment that wraps around the wick in order to heat the liquid on the wick. Local viscosity may be reduced via heating, while inhalation occurs, enabling atomization in the inhalation-generated flow of air 108. The e-Liquid 110 may be heated via an electric current flowing through the heating element 111 and may then be atomized and evaporated through the e-Cig and may contain tastes and aromas that create a smoking sensation. The controller 102 may be activated due to airflow 108 (from the inhaled air) passing a flow sensor 104. The sensor 104 may be activated by the pressure drop across the sensor and may directly switch the battery 106 power on, or be used as an input for the controller 102 that then switches the battery 106 current on. Although illustrated as separate from the e-Cig, the controller 102 may be a part of the e-Cig (e.g. along with the battery 106). The battery 106 may be a separate/removable assembly. The battery 106 may include one or more electronic chips controlling and communicating from it. It may connect with the cartomizer 113, which can be replaced or changed (e.g. when a new/different e-Liquid is desired).

The e-Cig may include two parts. The first part is often just referred to as the battery or battery portion (i.e. battery enclosure) and it includes the battery cell, the airflow sensor and the controller. The second part is the cartridge (i.e. cartomizer 113) includes the e-Liquid that is required for smoke and flavor generation. In other embodiments, there may be more or fewer parts. An airflow tube of the battery enclosure and an airflow tube of the cartridge may enable the smoker to puff through the e-Cig and activate the airflow sensor inside the battery portion. This may trigger the controller and cause the coil inside the cartridge to get hot, evaporate the liquid that is in the cartridge and cause smoke (i.e. vapor). The battery portion may instruct the cartridge to turn on, after which the coil is heated by the power applied by battery side (it may use a PWM scheme for controlling the heating profile).

Although not shown in FIG. 1, the e-Cig may include connections (i.e. connectors or electrical connections) that are used for power delivery to the heating element 111 and for charging the battery 106. In particular, that power delivery may be through metal connectors between the battery portion and the cartridge, such as those shown and described below with respect to FIGS. 3-4. The power (i.e. electrical current or electrical power) may be calibrated based on the measured temperature of the e-Cig. In one embodiment, an imager 120 may take images of the heating element 111 to determine if the temperatures within a heating element exceed a maximum temperature of if the temperature distribution within the heating element is not sufficiently uniform (i.e. there are hot spots). In one embodiment, the images from the imager 120 may be taken when the airflow is in a direction opposite the labeled airflow 108, such that a pump or vacuum at the battery end (e.g. near flow sensor 104) sucks air in the direction opposite labeled airflow 108. This embodiment is illustrated in and further described with respect to FIG. 4 (i.e. airflow 416). In addition, the imager 120 is also further described below with respect to FIG. 4 (i.e. imager 410 may be the same as or similar to imager 120). The analyzer 122 may analyze the resulting image to identify either of the potential problematic conditions (excessively high temperature or non-uniformity of temperature). In one embodiment, this identification may be used to calibrate the power because the presence of a problematic condition may require a slight decrease in power. The power may be decreased until the imaging reveals that the problematic condition is reduced or eliminated.

Although not shown, the e-Cig may include a non-volatile memory or memory chip in the cartridge. The memory chip may store information about the cartomizer, including the calibration information that may be transmitted to the controller 102 or battery 106 to set the power that is transferred to the cartridge. In particular, the calibration data can be read and conveyed to the controller (typically on the battery) that will apply the power regimen to the cartridge during smoking. This may be necessary because the cartridge is interchangeable with different battery portions and the calibration information may need to be conveyed to each battery portion for setting the appropriate power scheme for that particular cartridge. In another embodiment, the cartridge may include a communications chip that communicates to the battery (e.g. through a controller that may be a part of the battery portion or may be external to the e-Cig, such as a user's smartphone or other computing device that is in communication with the e-Cig). In another embodiment with a disposable e-Cig (e.g. both the cartridge and battery portion are disposable and may be one unit), the calibration testing may occur during production/assembly such that the calibration data may be used to set/adjust the power scheme at that time, which may eliminate the need for storing and/or communicating the calibration data. In alternative embodiments, the cartridge may be labeled with the calibration information which can be utilized by the user for establishing the power scheme.

FIG. 2 is a diagram of a portion of the cartridge of an electronic cigarette. FIG. 2 illustrates the heating coil 202 wrapped around a wick which is soaked with the e-Liquid. The heating coil is powered from the battery and the heat from the coil then operates to at least partially vaporize the e-Liquid (for generating the "smoke"). Image 204 illustrates an exemplary heat distribution (i.e. thermal image) of the wick and the coil. The heating coil should be below a maximum temperature and the temperature distribution across the coil should be uniform. A thermal image should illustrate an approximately uniform distribution of heat on the coil and the corresponding portions of the wick. In one embodiment, non-uniformity may be illustrated by "hot spots." The hotter spots on the wick may be more sensitive to burning, and when burning-inducing conditions may occur (e.g. when liquid flow is somewhat restricted), burning may be reduced if heat transfer more even (i.e. uniform distribution of heat/temperature). Any non-uniformity in the heating coil may exist if the temperature of a certain area of the coil is much higher than the average of the measured temperature.

FIG. 3 is a diagram of the coil and wick for an electronic cigarette. FIG. 3 illustrates the coil wrapped around the wick. The wick may include or be at least partially soaked with e-Liquid that is heated when the coil is powered. The coil is powered through two connecting wires that connect with the heating coil through crimping between the wires. As described a thermal image may indicate whether the coil and/or wick are below a maximum temperature and whether the temperature is uniform. In alternative embodiments, other components of the e-Cig, such as the crimping and connecting wires may also be imaged to check the temperature.

FIG. 4 is a diagram of an embodiment of imaging of an electronic cigarette. The wick 402 is wrapped with the coil 404 as shown in FIG. 3 with connecting wires 406, 408. The imager 410 may be the imager 120 from FIG. 1. The imager 410 may be connected with an analyzer (e.g. analyzer 122 from FIG. 1) for analyzing the thermal image. The thermal image direction 412 may be from a top portion of the heating coil 404 which is down from the mouthpiece end towards the battery portion. Imaging from this angle results in a thermal image of both the heating coil 404 and the wick 402. During the imaging a vacuum pump 414 may be located on an end towards the battery portion that establishes an airflow 416 that flows from the battery portion (not shown) towards the wick 402 and heating coil 404. In one embodiment, the analyzer analyzes a thermal image of the heating coil 404 to ensure the coil does not exceed a maximum temperature and to ensure that the heat distribution is uniform. In alternative embodiments, different imaging angles may be utilized for different components.

The imager 410 or 120 may be a measurement of infrared, such as infrared thermography ("IRT"), thermal imaging, or thermal video. The resulting images may be referred to as a temperature map or a thermogram. Since the amount of radiation emitted by all objects increases with temperature, the thermogram enables a visual depiction of temperature variation. In alternative embodiments, the imager may be an optical sensor/camera/recorder that includes an IR filter. The optical recording may be less expensive but the temperature measurements may be less accurate than with IR thermal imaging.

Figure 5:
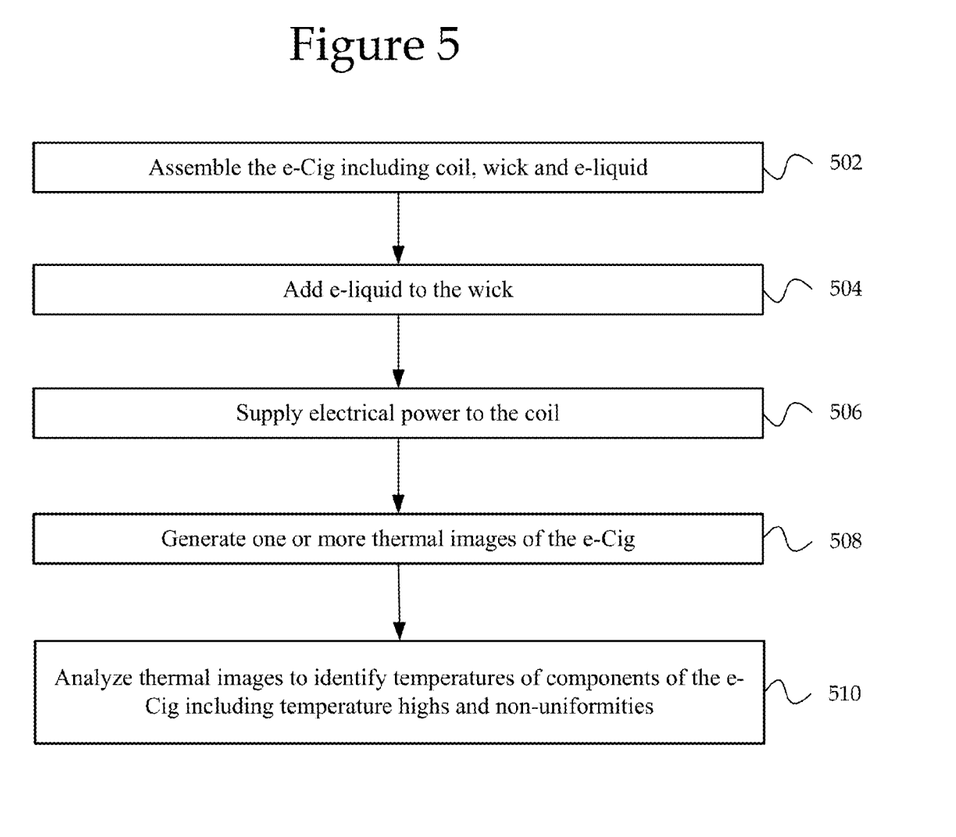
FIG. 5 is a diagram of an imaging process.

FIG. 5 is a diagram of an imaging process. As described, the imaging process may be utilized in the assembly process for checking components or calibrating components. A flaw in a component may be identified based on thermal imaging or proper calibration may improve the operation of the e-Cig. In block 502, the e-Cig is assembled including the cartridge (with coil, wick, and e-Liquid container). In one embodiment, the imaging is of a fully assembled e-Cig or at least a fully assembled cartridge, but in alternative embodiments, different components may be separately tested (e.g. the coil by itself may be tested prior to cartridge assembly). The e-Liquid from the e-Liquid container is added to the wick of the cartridge in block 504. Electrical power is then applied to the coil in block 506. Since the coil is powered, one or more thermal images may be taken of the assembly in block 508. As described with respect to FIG. 4, the thermal image may be of the coil and wick taken from the mouthpiece of the cartridge. In block 510, the thermal images are analyzed to determine the temperatures of components, such as the coil. There may be a preset maximum temperature and a preset uniformity threshold that are compared with the thermal image. In one example, the temperature uniformity may be a requirement that the temperature does not vary by more than X degrees across the coil, where the value of X may be preset. When the preset maximum temperature is exceeded or the analysis reveals that the temperature is not uniform, then there is a problem condition with the cartridge indicating either a faulty component or the need for calibration as described below with respect to FIG. 6.

Figure 6:
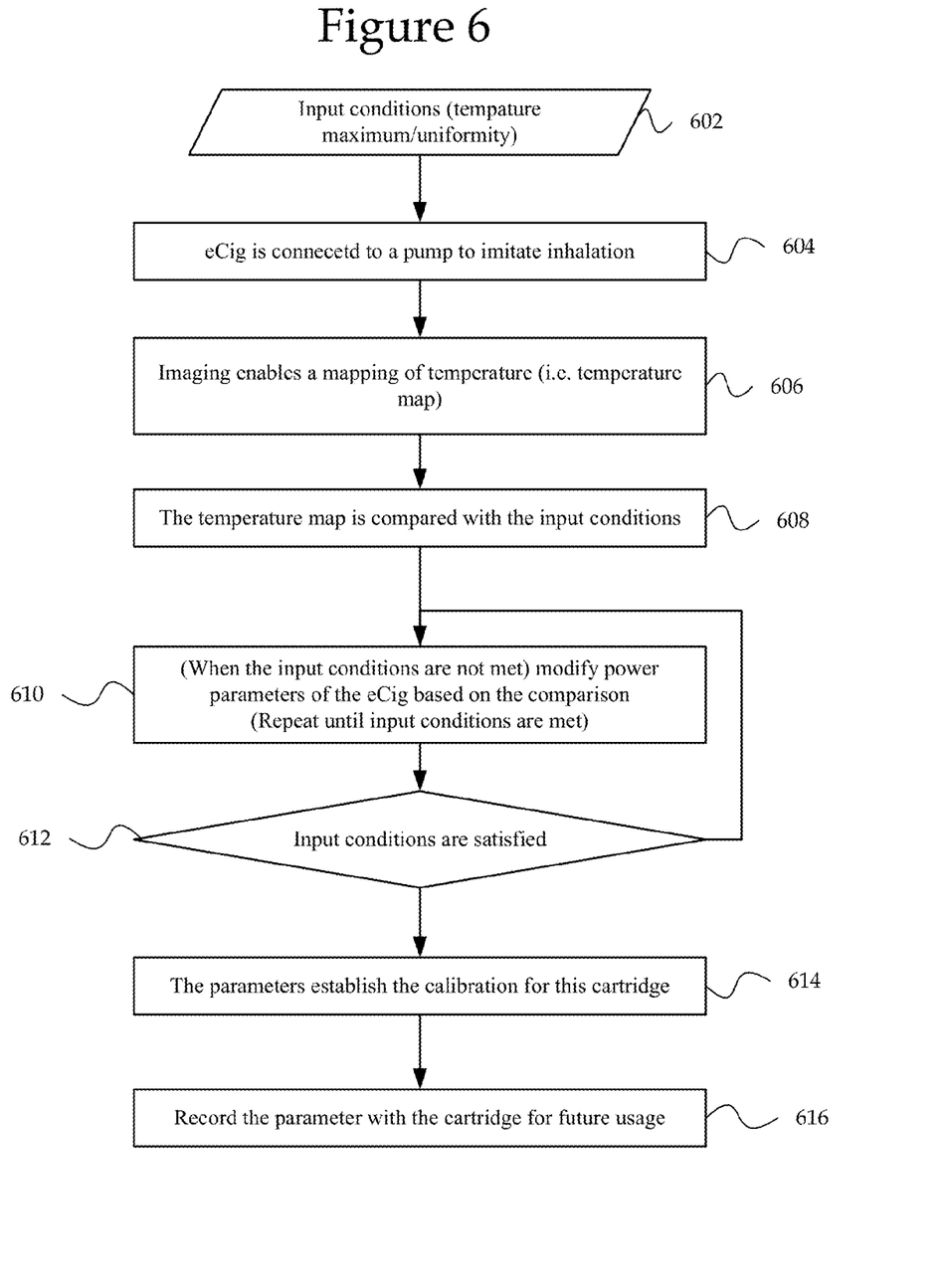
FIG. 6 is a diagram of a calibration process.

FIG. 6 is a diagram of a calibration process. In particular, thermal imaging may be used to calibrate a cartridge. The calibration can set a maximum power usage for a cartridge. In alternative embodiments, the calibration may be used for determining that a particular cartridge may require more limited usage (e.g. a break time after continuous usage). The calibration process may begin with input conditions for the analyzer in block 602. In one embodiment, the input conditions may include a maximum temperature (at any location) and uniformity of temperature required (e.g. limited variance of temperature). These input conditions are used for the analysis of a particular cartridge to determine if that cartridge may require calibration or adjustment of power usage for optimal usage. In block 604, the e-Cig is connected with a pump to imitate inhalation. In one embodiment, a vacuum pump is on an opposite end from the cartridge (e.g. battery portion) to "suck" air through the e-Cig. This inhalation imitation activates the e-Cig and the imager takes an image that maps the temperature of the imaged region (e.g. the heating coil) in block 606. The analyzer compares this temperature map with the input conditions in block 608 to determine any potential problem conditions. If there are no problem conditions identified, then the input conditions are satisfied in block 612. However, if the input conditions are not met, then the power parameters may be modified in block 610. In one embodiment, the modification of power parameters includes reducing the power provided to the cartridge. After the power is slightly reduced, another image may be taken and compared as in blocks 606-608 and if the input conditions are still not met then the process is repeated of slightly reducing power and checking the thermal image. After the input conditions are satisfied in block 612, the power parameters (i.e. the last power value that satisfies the input conditions) are established for the calibration in block 614. This parameter is then recorded with the cartridge for future usage in block 616.

The calibration may be for the PWM scheme. In an alternative embodiment, The calibration may modify the duty cycle (% on time vs. % off time) such that the calibration may include a shut off time that may switch off power periodically. For example, a particular cartridge may be limited to only 15 minutes of constant usage before requiring a temporary shut off. This may be in addition to or instead of the calibration of the power level described above with respect to FIG. 6. The calibrated power scheme may also include dynamically varying regimen parameters as a function of the battery charge (i.e. voltage) or any other complex energy management scheme.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

We claim:
1. A method for quality control of an electronic cigarette comprising:

powering a heating coil of the electronic cigarette;
generating a thermal image of the heating coil that includes a representation of a temperature of the heating coil;
analyzing the thermal image of the heating coil based on input conditions; and
calibrating the electronic cigarette based on the analysis of the thermal image of the heating coil.

2. The method of claim 1 wherein powering comprises providing electric current to a heating coil as part of an assembly process.

3. The method of claim 1 wherein the thermal image is an infrared image from an infrared camera.

4. The method of claim 1 wherein the thermal image is of the heating coil in a cartridge of the electronic cigarette.

5. The method of claim 4 wherein the calibrating comprises establishing an input power scheme for the cartridge.

6. The method of claim 5 wherein, when the analysis identifies either a non-uniformity or an excessive temperature, the calibrating comprises:
lowering a level of power provided to the cartridge; and
repeating the generating and analyzing until there is no identification of a temperature hot spot.

7. The method of claim 6 wherein a power scheme is determined, such that the power scheme includes the input power level when there is no identification of a hot spot.

8. The method of claim 6 wherein the cartridge includes a memory or communication chip for communicating the power scheme with a battery portion.

9. The method of claim 1 wherein the input conditions include at least one of a maximum temperature or uniformity of temperature.

10. An imaging system comprising:
an electronic cigarette cartridge including a heating coil;
an imager configured to generate a thermal image of at least the heating coil; and
an analyzer coupled with the imager and configured to analyze the thermal image based on input conditions to determine a requirement to calibrate the electronic cigarette cartridge.

11. The imaging system of claim 10 wherein the analyzer is configured to identify temperature variations across the heating coil, and determine whether or not a temperature across the heating coil is uniform based on the identified temperature variations.

12. The imaging system of claim 11 wherein the imaging system is configured such that determining that the temperature across the heating coil is not uniform triggers a calibration of the electronic cigarette cartridge, and the calibration includes lowering a level of power provided to the electronic cigarette cartridge.

13. The imaging system of claim 12 wherein,
the imaging system is configured to repeat the image generation and analysis until the temperature across the heating coil is determined to be uniform; and
the imaging system is configured to record at least one power parameter of the electronic cigarette when the temperature across the heating coil is determined to be uniform.

14. The imaging system of claim 13 wherein the electronic cigarette cartridge includes a memory or communication chip that communicates calibration information including the at least one power parameter to a battery portion.

15. The imaging system of claim 11 wherein the imager includes an infrared thermal imager.

16. The method of claim 1, further comprising:
identifying a potential burning location based on the thermal image,
wherein the calibrating the electronic cigarette includes calibrating a cartridge of the electronic cigarette when the potential burning location is identified.

17. The method of claim 16 wherein the identifying a potential burning location includes identifying a substantial non-uniformity of the temperature throughout the coil or identifying a relatively higher temperature at any location on the coil.

18. The method of claim 16 wherein the calibrating the electronic cigarette includes adjusting electric current to the coil when the potential burning location is identified until the calibrating the electronic cigarette results in no identifying of a potential burning location.

19. The method of claim 18 wherein the heating coil is provided in the cartridge, and the cartridge includes a memory device or communications device for communicating with a battery portion to establish the electric current to the coil.

* * * * *